United States Patent [19]
Morgan

[11] Patent Number: 5,459,323
[45] Date of Patent: Oct. 17, 1995

[54] MEASUREMENT OF LUMINESCENCE

[75] Inventor: Christopher G. Morgan, Irlam, United Kingdom

[73] Assignee: University of Salford, United Kingdom

[21] Appl. No.: 927,504

[22] PCT Filed: Jan. 14, 1991

[86] PCT No.: PCT/GB91/00046

§ 371 Date: Sep. 11, 1992

§ 102(e) Date: Sep. 11, 1992

[87] PCT Pub. No.: WO91/10897

PCT Pub. Date: Jul. 25, 1991

[30] Foreign Application Priority Data

Jan. 12, 1990 [GB] United Kingdom ............... 9000740

[51] Int. Cl.$^6$ ............................................... G01N 21/64
[52] U.S. Cl. .................................................. 250/458.1
[58] Field of Search .................................... 250/458.1

[56] References Cited

U.S. PATENT DOCUMENTS

| | | | |
|---|---|---|---|
| 4,200,801 | 4/1980 | Schuresko | 250/458.1 |
| 4,845,368 | 7/1989 | Demas et al. | 250/459.1 |
| 4,937,457 | 6/1990 | Mitchell | 250/458.1 |

FOREIGN PATENT DOCUMENTS

| | | | |
|---|---|---|---|
| 229220 | 10/1985 | German Dem. Rep. | 250/458.1 |

OTHER PUBLICATIONS

Journal of Physics E: Scientific Instruments vol. 19, No. 5, May, 1986 The Institute of Physics, (GB), J. C. Murray et al., pp. 349–355.

Review of Scientific Instruments, vol. 45, No. 3, Mar. 1974, The American Institute of Physics, E. W. Schlag et al., pp. 364–367.

Review Scientific Instruments, vol. 58, No. 9, Sep. 1987, American Institute of Physics, W. G. McMullan et al., pp. 1626–1628.

Applied Optics, vol. 21, No. 13, Jul. 1982, Optical Society of American (New York, US), T. Murao et al., pp. 2297–2298.

Applied Physics Letters, vol. 46, No. 4, Feb., 1985, (New York, US) A. Z. Genack, pp. 341–343.

*Primary Examiner*—Constantine Hannaher
*Attorney, Agent, or Firm*—Rockey, Rifkin and Ryther

[57] ABSTRACT

Apparatus for producing decay time weighted information (e.g. a decay time weighted image) of a luminescent sample, comprises an excitation light source arranged to illuminate the sample, means for modulating or pulsing the intensity of the excitation light in a predetermined cyclical manner, detector means for detecting photons emitted by the sample as a result of luminescence, means for storing data representative of detected photons, the stored data being weighted as a function of phase difference between detection of photons and the cyclically varying modulation, and means for producing decay time weighted information from the stored data.

20 Claims, 11 Drawing Sheets

MEASUREMENT OF LUMINESCENCE

The present invention relates to the measurement of luminescence (e.g. fluorescence of phosphorescence), and more particularly to the measurement of luminescence decay times.

Reference in the following description is made to fluorescence decay times, but the description is also applicable mutatis mutandis to other forms of luminescence.

Fluorescence microscopy is very widely used in modern biology, forensic science and materials analyses, as well as in many other areas. Fluorescence is sensitive in two senses. It can be detected with very high sensitivity, and emission (and sometimes excitation) parameters are very environmentally sensitive. The environmental sensitivity leads to the use of fluorescent probes to monitor local environment (pH, oxygen, tension, concentration of important ions such as calcium, etc.). However, this sensitivity also leads to a potential ambiguity, in that fluorescence intensity depends on concentration of fluorophore, excitation intensity and quantum yield of said species. Thus, it is not possible to directly relate concentration of fluorophore to measured intensity, even where excitation intensity is constant, unless the quantum yield is also known to be constant within a sample. For many fluorescent samples, especially those studied by fluorescence imaging (e.g. microscopy), variation of quantum yield within a sample is common. Ideally one would wish to have a means of measuring not only fluorescence intensity, but also quantum yield. Generally this is a very difficult problem. However, in many circumstances one can infer fluorescence quantum yield from a measurement of fluorescence decay time. Where this is not valid, this implies a change in the radiative lifetime (the decay time in absence of all extraneous deactivating processes, which is an intrinsic property of the fluorescent species related to the fluorescence efficiency). Such changes are usually detectable, since the perturbations which change radiative decay time also influence spectroscopic properties of excitation and/or emission.

Fluorescence decay times are usually measured using one of two techniques. The most common is the time-correlated single photon counting method where fluorescence is excited using a repetitive source of short optical pulses (1). An alternative method uses phase-shift/demodulation measurements of fluorescence emitted in response to an amplitude modulated excitation source (2). In the latter technique, it is necessary to make measurements as a function of modulation frequency if the fluorescence decay is not a single exponential.

The choice between the time and frequency-domain approaches to fluorescence decay measurement is largely governed by practical considerations such as availability of equipment. However, there are clear sets of circumstances where one or other method finds favour. If the fluorescence can be excited conveniently by the output of a low cost laser (such as the green Helium Neon or Argon ion laser), then the phase shift/demodulation approach is particularly convenient, since laser output is easily modulated with a Pockels cell (3), and some lasers have built-in provision for amplitude modulation. Where laser excitation is not convenient, phase methods become more difficult. Light from an arc source can be modulated using Pockels cell, but only at the expense of very low throughput due to stringent collimation requirements. When a wide wavelength range is desired, the necessary Glan Taylor polarisers attenuate the beam further.

If an arc source is projected through a Pockels cell, a characteristic pattern is seen composed of a pair of cusps coming together at a central point to form a cross. Application of a voltage to the Pockels cell causes these cusps to move apart, so that by using a small central aperture as a spatial filter it can be arranged that the intensity of light passing through the aperture is modulated if a fluctuating voltage is applied to the device. The appearance of the projected pattern is a consequence of light passing through the modulator assembly off-axis, and homogenous modulation is only possible for extremely well collimated light such as that from a laser. Use of an arc source is particularly convenient in respect of its continuous output and wavelength tunability, so that the difficulty in efficiently modulating such a source is most unfortunate. The tradeoff between high modulation depth and light throughout cannot be avoided if a Pockels modulator is used, and this is generally favoured over optical alternatives because of wide modulation bandwidth.

As an alternative to modulation using an optical element, in some cases output of a light source can be directly modulated.

In order to minimise the disadvantage of relatively low intensity excitation when using a Pockels cell with an arc source, the sensitivity of fluorescence detection must be as high as possible. Even where adequate exciting light intensity is available it is usually desirable to optimise detection sensitivity, for example to minimise photodamage to the sample. To this end, it is particularly convenient to use single photon counting detection. In a previous paper (4), we have described one means of using single photon counting detection with phase/modulation fluorometry. This approach used Fast Fourier Transform (FFT) analysis of a histogram data set resulting from multichannel analysis of output from a time-to-pulse height converter.

An alternative approach to phase shift measurements using photon counting has been described, based on digital correlation (5). In this technique a square wave 'gate' at the modulation frequency is used to direct signals between two high frequency counters. The phase of the square waveform can be adjusted to maximise the counts ratio between the two counters, and hence the phase of the emission can be readily measured. This approach is simpler and cheaper than that outlined in (4), and is capable of counting at higher rates. In its original form, however, it suffers from the disadvantage that errors will be generated if the excitation source is not a pure sinusoid.

According to the present invention there is provided apparatus for producing decay time weighted information of a luminescent sample, comprising an excitation light source arranged to illuminate the sample, means for modulating or pulsing the intensity of the light source in a predetermined cyclical manner, detector means for detecting photons emitted by the sample as a result of luminescence, means for storing data representative of detected photons, the stored data being weighted as a function of phase difference between detection of photons and the cyclically varying modulation, and means for producing decay time weighted information from the stored data wherein the weighted stored data is obtained using two reference signals each varying in a predetermined cyclical manner and having a known phase shift relative to each other.

The invention is particularly applicable to the production of decay time weighted images but may be used for providing other types of decay time weighted information, e.g.

time resolved fluorescence depolarisation measurements, differential polarised phase shift measurements, and measurements of time dependent changes in fluorescence decay parameters as well as conventional fluorescence decay time measurements. Some embodiments of the invention (e.g. the imaging arrangements described below in relation to FIGS. 5 and 10) are especially adapted for spectrally dispersed array detection such as measurements of excitation emission matrices wherein the decay time related parameters of excitation and emission are represented.

The phase relationship between the signals and the modulation of the light source should be known, and preferably one of the reference signals is in phase with said modulation (which may be in the radio-frequency range). Preferably the reference signals are in quadrature relative to each other.

Preferably the reference signals and the modulation of the excitation source are sinusoidal.

Preferably the detector is capable of detecting single photons. The detector may for example be a photomultiplier or, more preferably, an imaging photon detector (an example of which will be described in more detail below). The photon related output signal of such a detector is preferably compared with each of the reference signals in such a way that this photon related signal produces an output from the comparison with a probability which is dependent on the time position of the output relative to the maxima of the wave. Such an output signal may then be used to build up a representation of an image, as discussed more fully below.

In an alternative embodiment, the detector may comprise an image intensifier associated with an electronic camera. Images may be obtained by modulating the voltage between the photocathode (of the intensifier) and the front of the micro-channel plate, or alternatively the gain of the detector may be varied by other means such as variations of voltage across the micro-channel plate, or on a suitably positioned grid or electrode within the intensifier. An image intensifier not including a micro-channel plate such as an intensifier diode tube may also be used and modulated by varying the accelerating voltage within the tube. Alternatively, a detector system which might or might not include an intensifier may be used, preceded by an optical element, the optical transmission of which can be modulated. One image may be obtained with this voltage being modulated in phase with the modulation of the excitation source, and another image obtained with this voltage being modulated in quadrature (with the modulation of the excitation source). In practice it is convenient also to generate an image where the detector modulation and excitation modulation are in antiphase, since the subsequent image manipulations required for decay time contrast are preferably conducted after subtract of a 'DC' component from the image, and this component of the image is generated most simply by averaging 'phase' and 'antiphase' images.

Preferably the light source is directly modulated giving sinusoidally fluctuating emission with low harmonic content.

Most preferably, the light source is a deuterium lamp adapted for radio frequency modulation, which source gives good wavelength tunability, low harmonic content and very high temporal stability.

The invention will be further described by way of example only with reference to the accompanying drawings in which.

Figure 5:
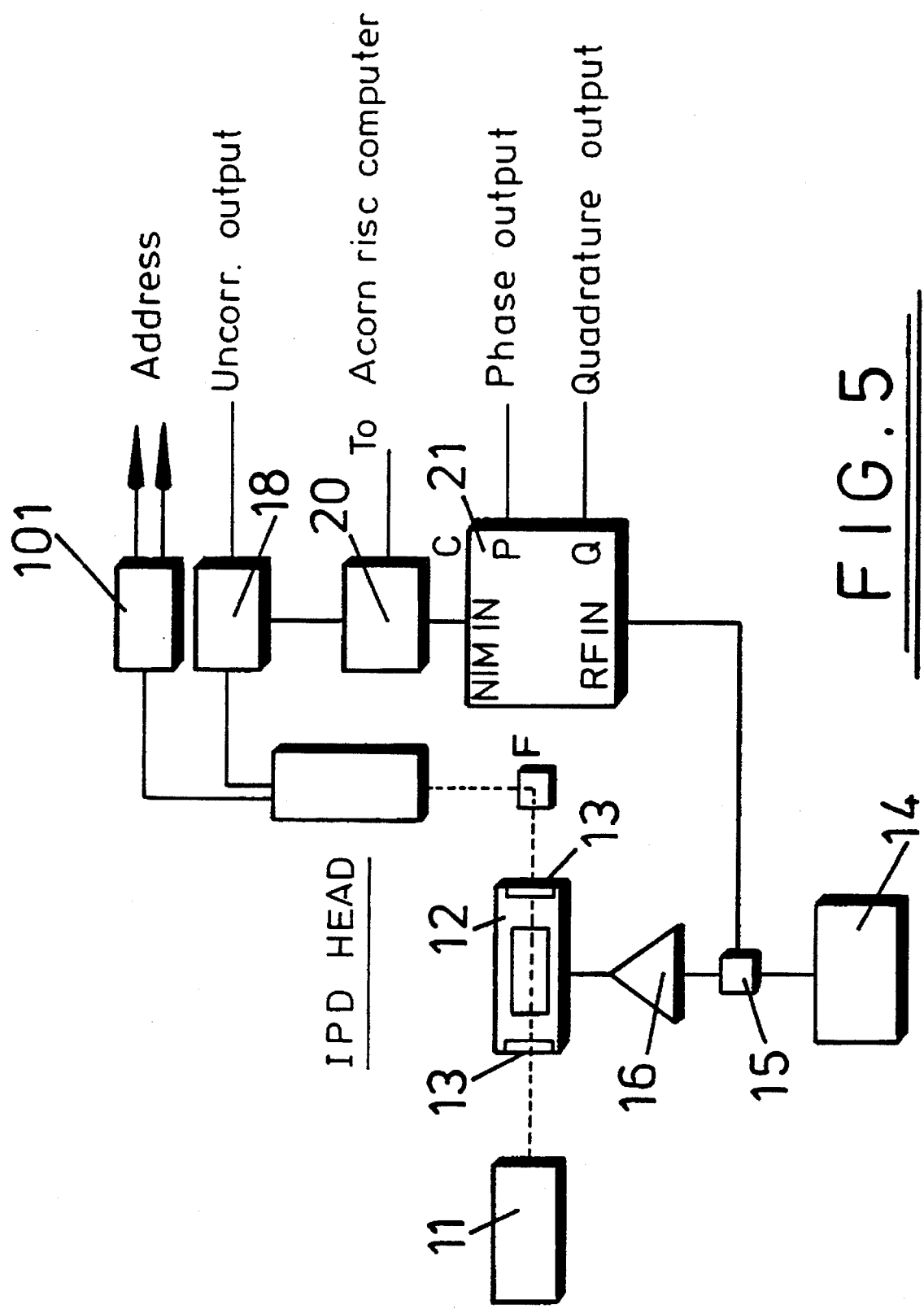
FIG. 5 is a second embodiment of the invention based on the use of an Imaging Photon Detector.
Figure 6:
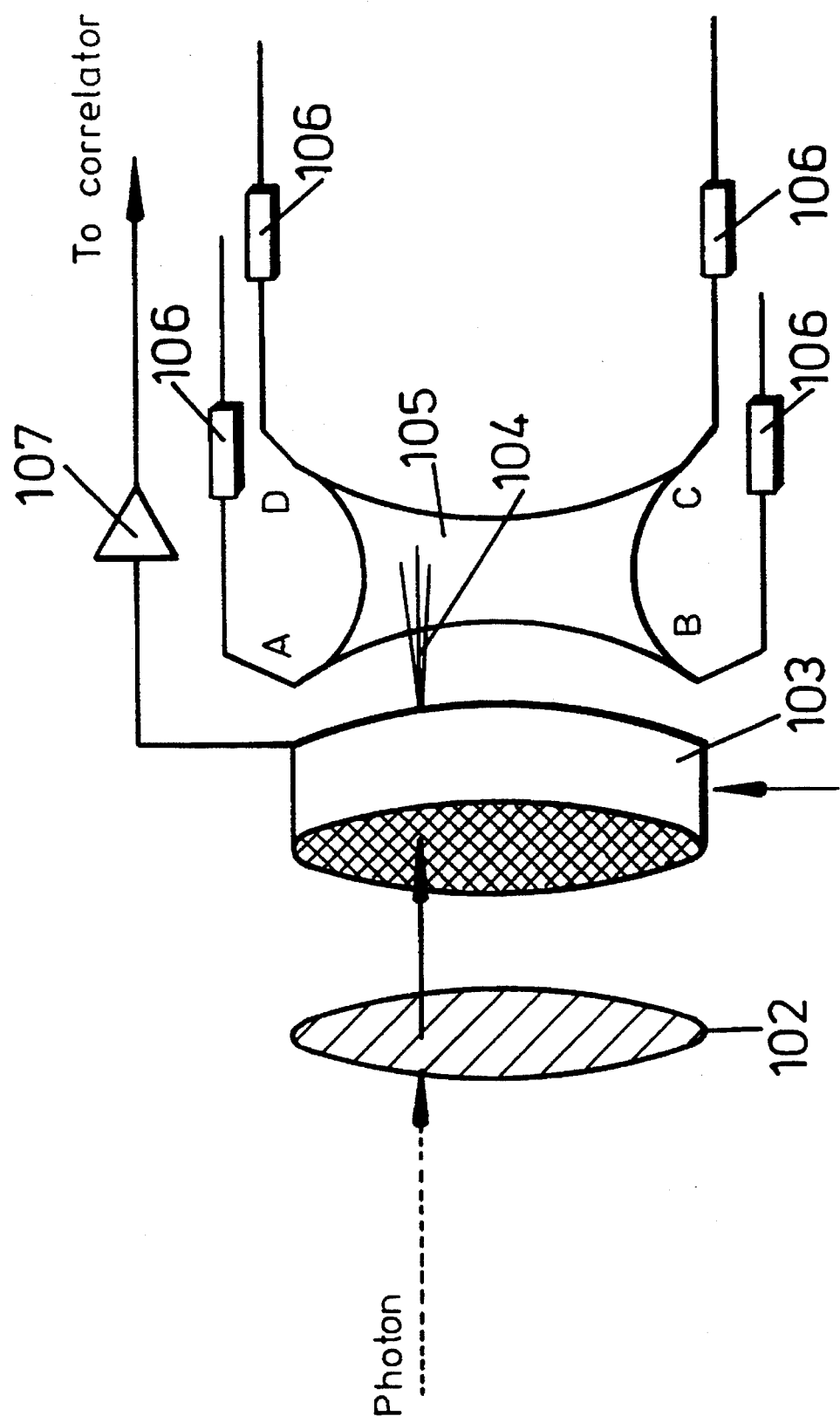
Figure 7A:
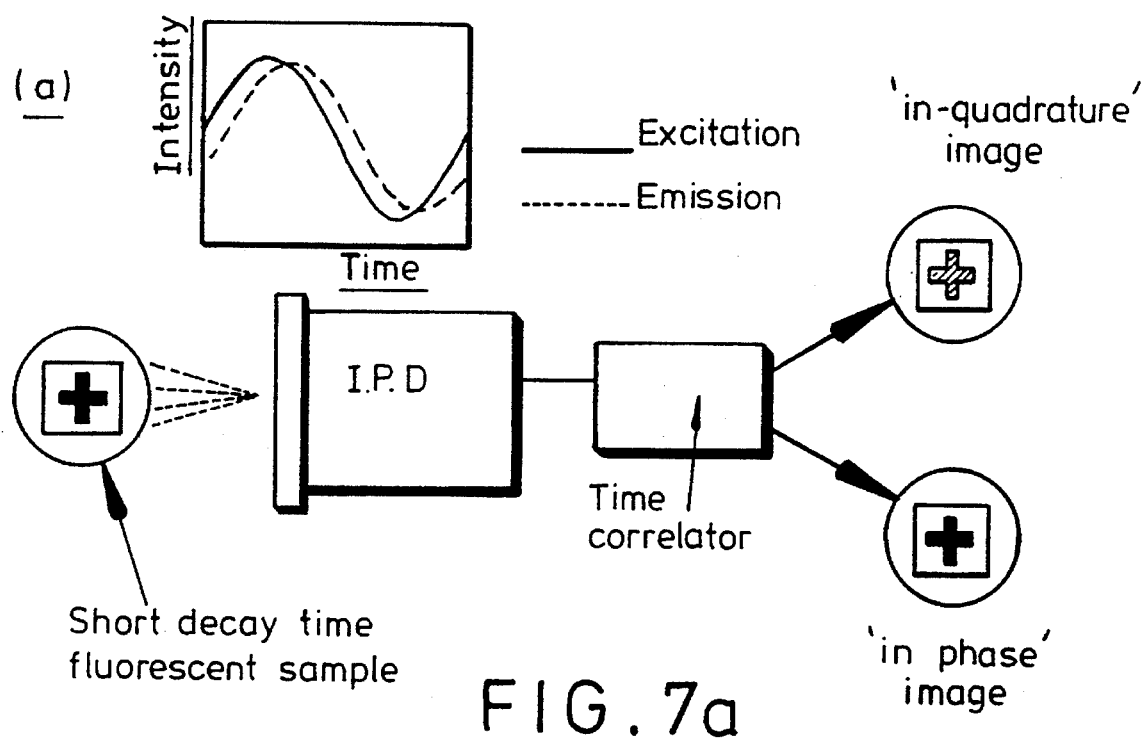
Figure 7B:
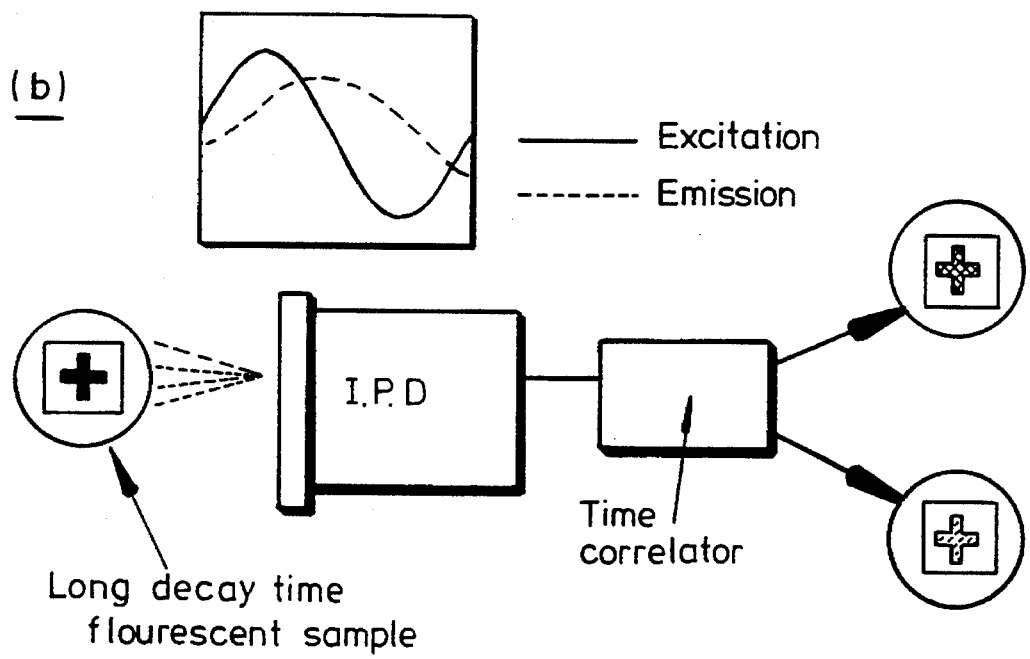
Figure 8:
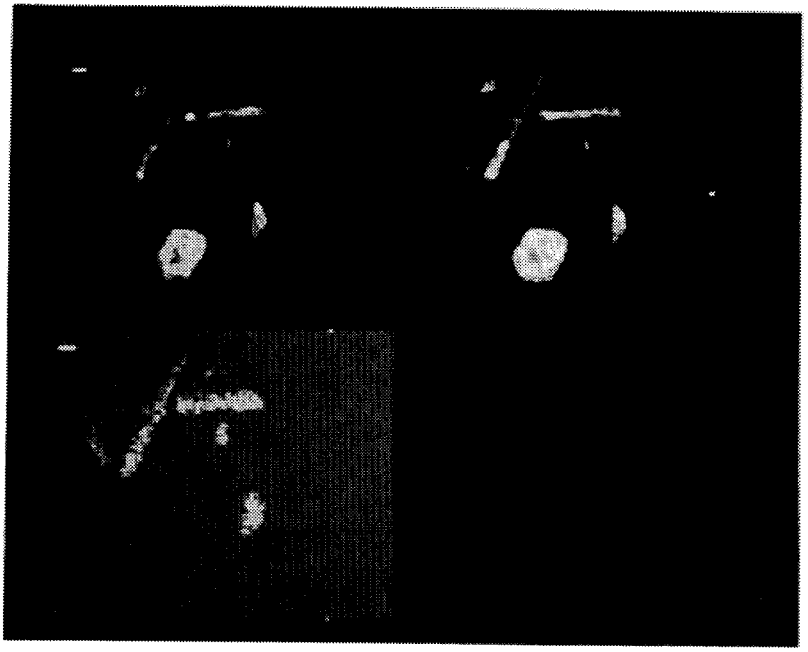
Figure 9:
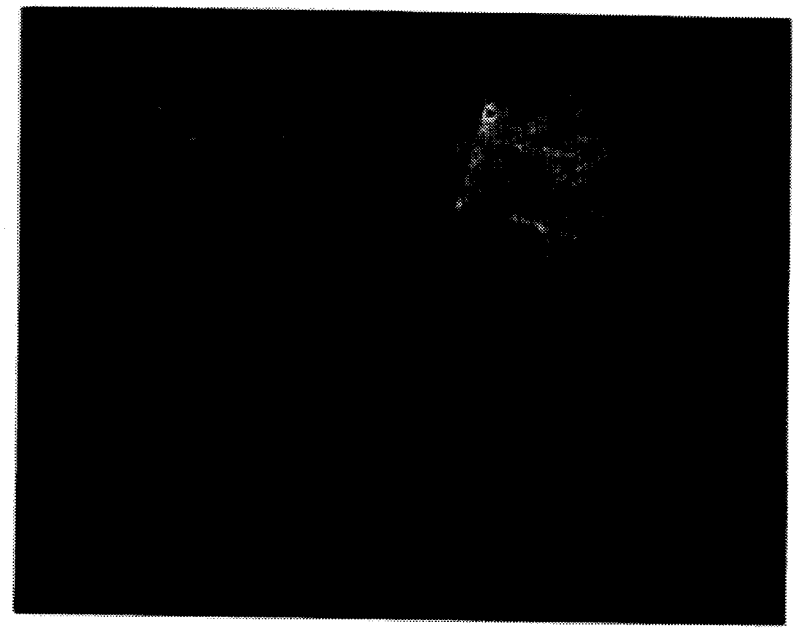
Figure 10:
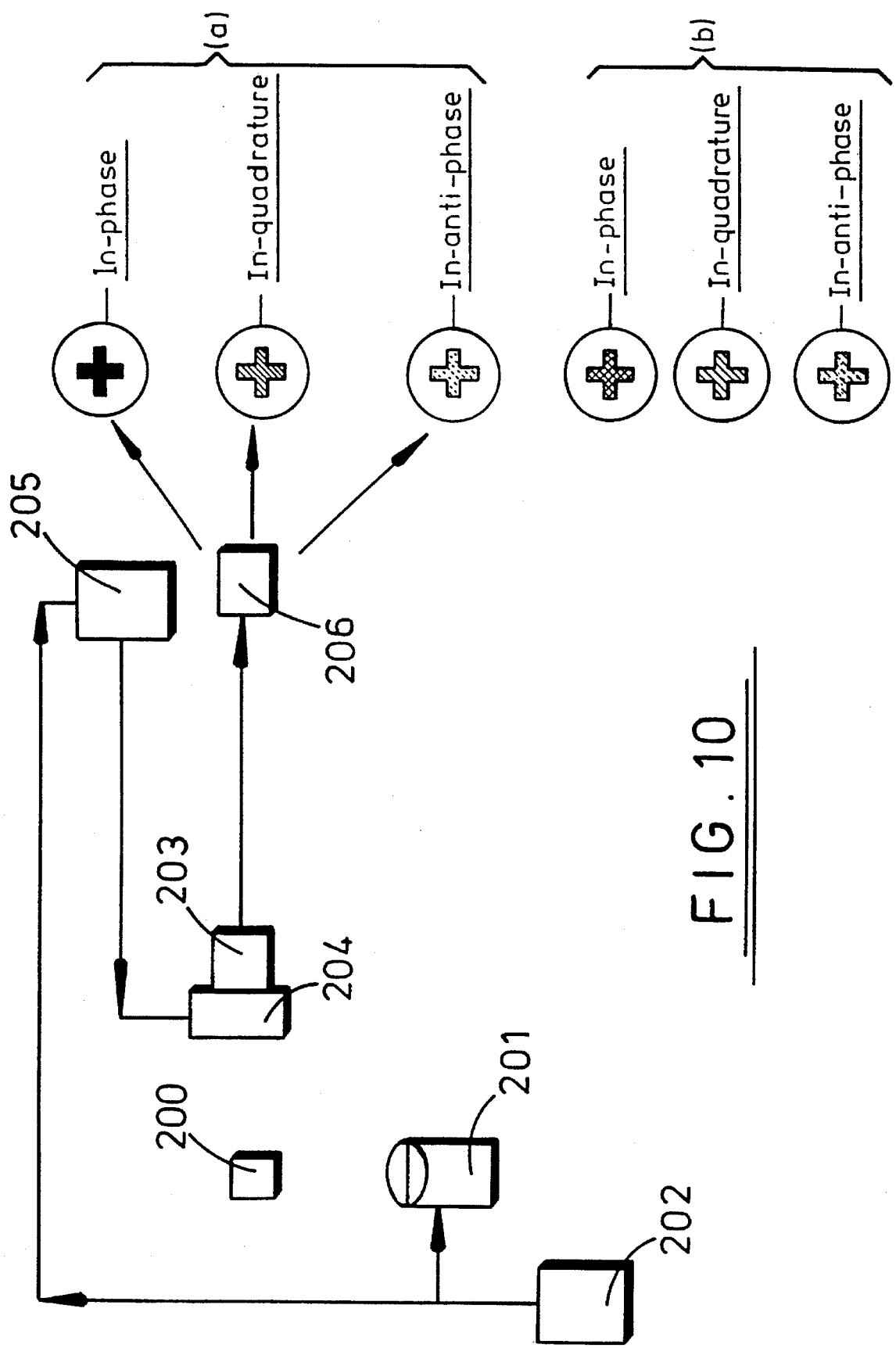

FIG. 6 schematically illustrates the detection arrangement employed in the Imaging Photon Detector used in the apparatus of FIG. 5;

FIGS. 7a and 7b schematically illustrate the results obtained using the apparatus of FIG. 5;

FIGS. 8 and 9 are photographs of computer generated images obtained using the apparatus of FIG. 5;

FIG. 10 schematically illustrates a third embodiment of the invention based on the use of an Intensified CCD camera; and FIGS. 11(a), 11(b), 12(a), and 12(b) are photographs of computer generated images obtained using the apparatus of FIG. 10.

Figure 1:
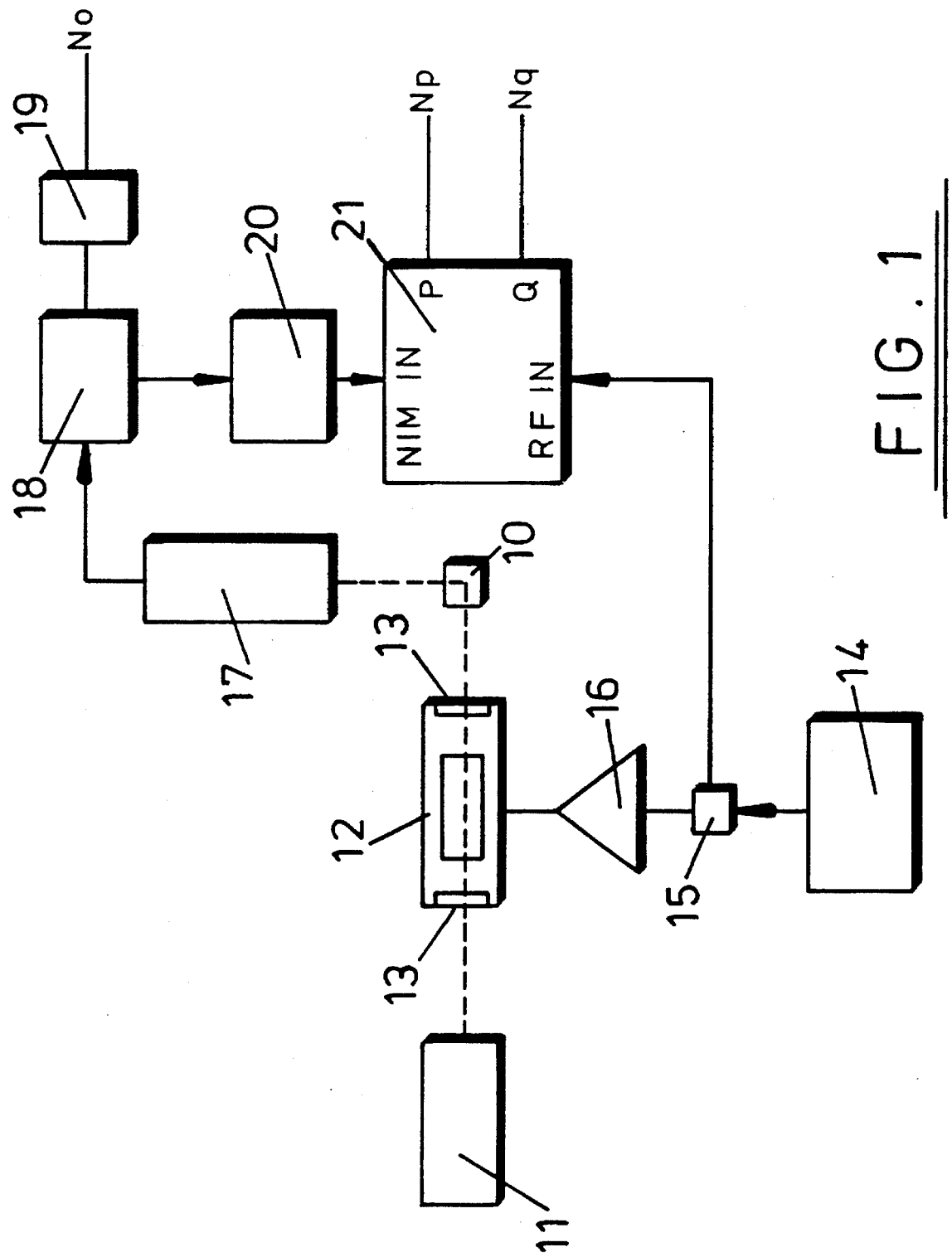
FIG. 1 is a block diagram of the first embodiment of the apparatus in accordance with the invention based on the use of a single photon counting photomultiplier.

The embodiments of FIGS. 1 and 5 incorporate detectors which count individual photons. For such detectors (counting individual photons) a photon correlation module is a central feature of frequency domain decay time measurements based on the detectors. Therefore before describing the embodiments of FIG. 1 the operating principles of one such correlator will be described below.

Basically, the problem is how to measure the phase shift and demodulation of a light source (e.g. a fluorescing compound) when the signal reaching the detector is so weak that only individual photons are seen at discrete intervals. To explain the principles, it is worth considering how one might measure the phase shift and demodulation if the signal were continuous (i.e. a photocurrent where statistical fluctuations could be ignored). One approach is to measure the Fourier sine- and cosine transforms at the fundamental frequency. The required information can then be measured since the phase shift (relative to the fixed reference) is given by measuring the arc tangent of the ratio of sine to cosine transforms, while the demodulation is calculated from the RMS value of the transforms. To implement a sinusoidal transform, the signal is multiplied by the appropriate sinusoid, integrated over a fixed time, and any average ('DC') component subtracted. Thus, for a photocurrent phase measurement, one would use, e.g. a fast RF mixer for a multiplication and integrate over time in a filter, subtracting out a component measured with no such multiplication (as 'DC' component).

To accomplish the same for a probabilistic representation of a signal, as in an output from a photon counter, the principle is similar. The probability of a given photon-derived pulse being accumulated in a computer memory (integrated) must be made to fluctuate sinusoidally.

For phase and demodulation measurements, a sine- and a cosine transform are needed. To allow for this, the correlator module has two channels and an incoming pulse is discriminated and identical pulses are simultaneously presented to each channel.

The system is shown in block diagram form in FIG. 1.

Fluorescence of a sample 10 is excited by light from a mercury arc lamp source which has been passed through a Pockels cell modulator 12 associated with Glan Taylor polarisers 13 as shown. Modulation of the light passing through the Pockels cell 12 is effected by means of a Radio Frequency source 14 which supplies an RF signal to the cell 12 via an RF splitter 15 and an RF power amplifier as shown. Thus the light impinging on sample 10 is modulated at Radio Frequency and the sample 10 is caused to fluoresce.

Although FIG. 1 illustrates the modulation of a light

'beam', it would also be possible to use a light source (e.g. a deuterium lamp) which could itself be modulated. Thus if a modulated light source is employed, there is no need to employ the Pockels cell 12, the modulation being applied directly to the source.

Fluorescence is detected by a photomultiplier 17 which is a single photon counting device.

Each photon detected by the photomultiplier 17 produces an output pulse which is processed using a Constant Fraction Discriminator 18 (ORTEC 473A). The Constant Fraction Discriminator produces an output only if the pulse from the photomultiplier 17 is above a particular peak height (thus discriminating against noise from the photomultiplier which would produce pulses of lesser amplitude). Additionally the output of the Constant Fraction Discriminator is only triggered at a constant fraction of the peak height of the input pulse from the photomultiplier 17, thereby minimizing "jitter". The output of the Constant Fraction Discriminator is a NIM (Nuclear Instrumentation Module) timing pulse.

The output of the CFD is split, with a first output being passed to a frequency counter 19 allowing the average photon counting rate $N_O$ to be recorded.

A second, coincident discriminator output is fed through a variable delay line 20 to the photon input of a correlation module 21 which also receives a synchronizing signal derived from the RF modulating voltage.

Within the correlation module 21, the NIM pulse is compared with two signals, one of which is in-phase with the RF modulation (provided by source 14) and the other of which is in quadrature relative thereto. The object of the comparison in each channel is to allow photon-related pulses to "pass through" (i.e. to trigger an output pulse from the given channel) with a probability which is dependent on their time position relative to the maxima of the RF signal applied to the channel. A photon pulse which arrives when the RF is at its peak has greatest probability of acceptance, while one which arrives when the RF is at a minimum has lowest probability. Photons arriving at intermediate times have probability of "passage" which is linearly proportional to the RF signal at the instant of arrival.

An alternative explanation of the correlator is as follows. The detector is capable only of detecting photons emitted from the sample, and not of discriminating between photons emitted by the short and long decay time species. It is the correlation with the in-phase and in-quadrature signals which provide this discrimination. The modulation of the exciting light is preserved in fluorescence emission to an extent which decreases as the fluorescence decay time increases. Similarly the maximum brightness of emission is displaced in time (i.e. phase shifted) relative to excitation by an extent which increases as decay time increases. The in-phase channel of the correlation effectively weights data so that events occurring close in time to the peaks of excitation intensity are most likely to be recorded. Similarly, the quadrature channel biases detection to a time which is delayed relative to the excitation maxima so that events which are delayed relative to the peaks of excitation are most likely to be recorded.

For each channel, if photon-generated pulses are applied from an unmodulated source then on average fifty percent of these pass through. If however, light from a source modulated at the RF input frequency generates the signals then the actual number of pulses passing through the channel depends on the depth of modulation and phase relative to the RF input to the channel. Since this correlation only holds true if the modulation frequency and the RF input to the channel are identical, any harmonics in the modulated signal are rejected. Since two channels are provided driven in quadrature, the phase angle of modulation is easily determined by comparison of the time averaged counts passed by each, these counts being represented in FIG. 1 as $N_p$ for the 'in-phase' channel and $N_q$ for the channel in quadrature. All that is required is to subtract from each count the value obtained using unmodulated light (i.e. the 'DC' component, D), and calculate the ratio of residual counts. The residual count from the channel driven in phase with the signal driving the light modulator is effectively the 'real' part of the Fourier component (Re) of the signal. Similarly, the residual count from the 'quadrature' channel is the 'imaginary' part of the Fourier component (Im). As is well known, the phase angle ($\phi$) of a signal is simply given by Tan ($\phi$)=Im/Re. The depth of modulation (M) is also easily determined as $$M=((Re)^2+(Im)^2)^{1/2}/D.$$

Errors arising due to changes in light intensity may be eliminated by using the frequency counter in ratio mode. The ratio of phase or quadrature-correlated counts to total photon counts is then used in all calculations.

Figure 2:
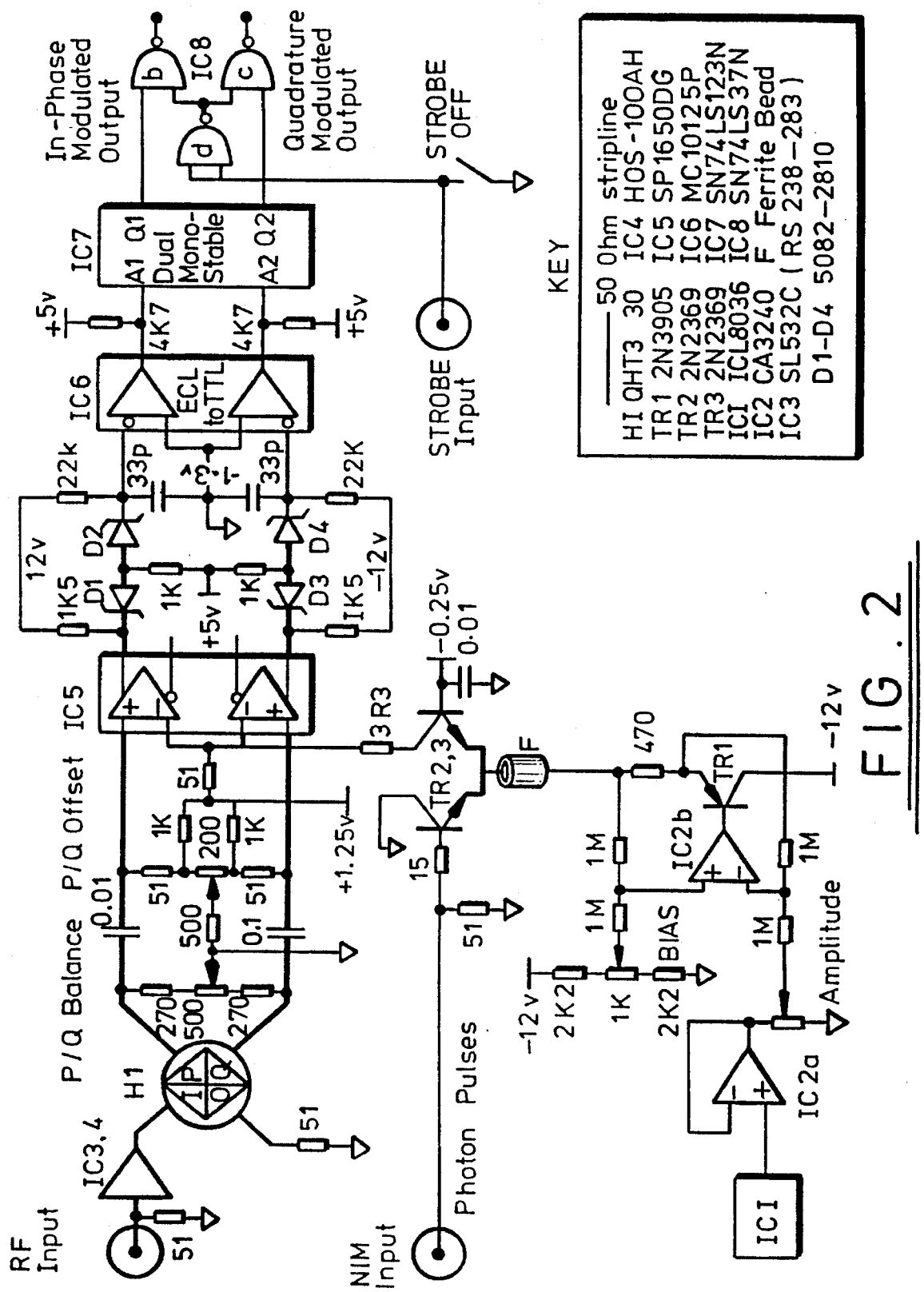
FIG. 2 is a correlation circuit for use in conjunction with the apparatus of FIG. 1.

One example of correlation circuit 21 is illustrated in FIG. 2.

Operation of the correlator requires modulation of the probability of a pulse propagating through the channel. To achieve this, the fixed amplitude pulses originating from the photon-counting discriminator are applied to a fast current-gate consisting of transistors TR2, TR3. Current is applied to the gate from a low frequency triangular-wave generator (IC1, IC2, TR1) which has no fixed phase-relationship to the radio-frequency source driving the light modulator. The output of the gate is a series of negative pulses with a range of amplitudes within a triangular envelope; i.e., all amplitudes in this range are equally represented in a sufficiently long-time sample. These amplitude-modulated photon pulses are applied to a pair of fast-comparators (IC5), biased to allow 50% of the pulses to trigger each channel in the absence of any other input.

A radio frequency signal, synchronous with the light modulation, is amplified to about 600 mV pK-pK and applied to 90-degree Power Divide (Merrimac QHT3-30) which produces two outputs, nominally in quadrature. Each of these RF signals provides the complementary input to a comparator, and linearly modulates its threshold. The probability of a photon-generated pulse passing through the channel is thus directly correlated to the amplitude of the RF signal at the instant of arrival of the pulse.

The Quadrature Divider outputs can be balanced in amplitude over the bandwidth of the device (25.5 to 34.5 MHz) using trimpot RV1. Power reflected from this network is conveniently absorbed in Port 4 termination. Differential offset between the two comparators can be nulled using trimpot RV2. Each comparator drives an identical logic chain consisting of a pulse stretcher (D1, D2, etc.), ECL to TTL converter, monostable and gated inverter output. That part of the circuit dealing with fast pulses and RF signals is laid out using ground plane and 50 ohm strip-line techniques. Care has been taken to ensure symmetry between the two channels, and to minimise cross-coupling between the main circuit blocks.

The essential features of the circuit is that a deterministic event (i.e. the presence or absence of a photon-generated pulse) is converted into a probabilistic process; if pulses were not first assigned to a uniform spread of amplitudes between two levels, the final discriminator could only accept or reject the pulses in a binary fashion, depending on the RF level. The key point is that the triangle waveform which results in pulses having the required amplitude spread is not related to the RF signal and so the assignment of pulse amplitude is totally uncorrelated to the light modulation.

Figure 3:
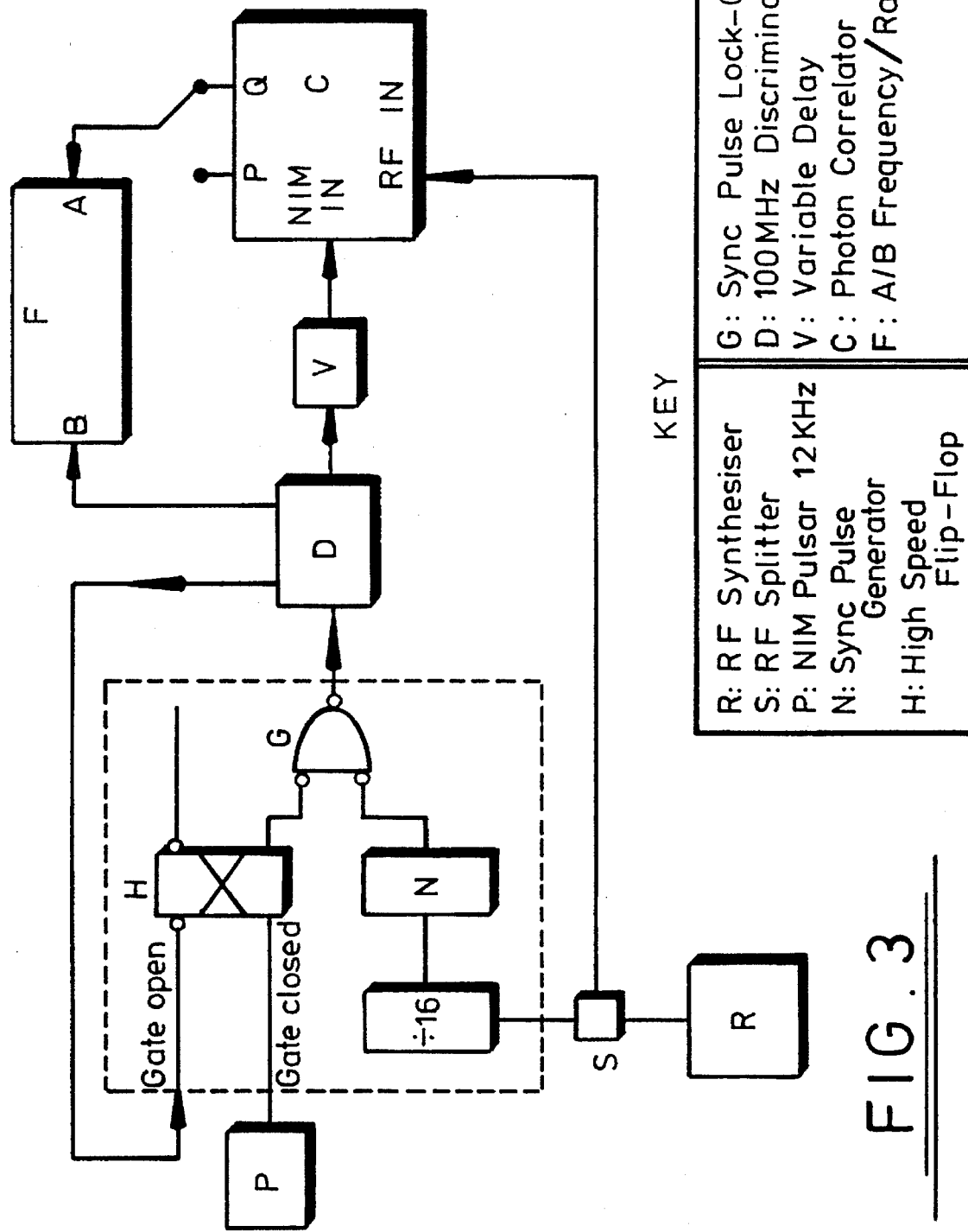
FIG. 3 is a test circuit arrangement.

In practice, an arbitrary phase difference exists between the modulation reference signal applied to the correlator and the actual modulation in rate of photons recorded, due to shifts in the RF amplifier, Pockels Cell Modulator and detection electronics. A complete profile of the modulated emission can be obtained by stepping the variable delay. FIG. 3 shows a test circuit arrangement whereby simulated "photon pulses" are produced, synchronous with the RF signal, but rate-reduced to the pulser frequency of 12 KHz. The pulse lock-out gate used in this setup has been developed to enhance the precision of the data collection from our Fourier Transform Microfluorometer (4). The gate is opened by a random ("photon") event, allowing RF synchronous pulses to pass. The first 'sync' pulse detected closes the gate again; thus only one RF pulse is obtained for each random pulse received.

Figure 4:
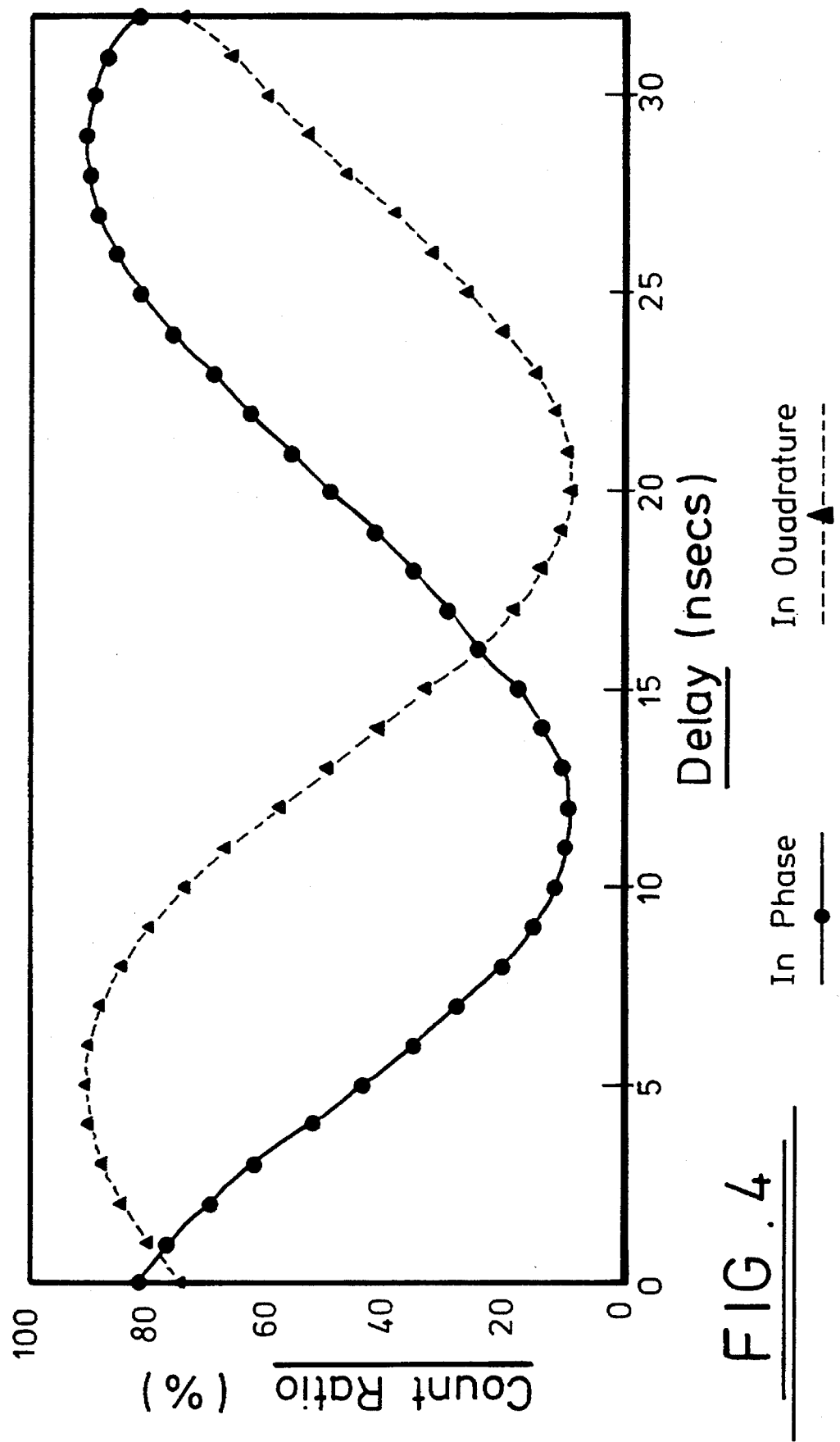
FIG. 4 shows calibration curves.

Phase and Quadrature correlation ratios of these test pulses were recorded as a function of delay setting, and FIG. 4 shows a typical calibration. It can be seen that four factors must be controlled to give optimum correlator performance:

a) bias adjusted to give 50% acceptance of uncorrelated events, b) amplitude chosen to fully utilize the linear range of correlation, c) phase and quadrature relative amplitudes balanced, d) phase-quadrature differential offset reduced to zero.

These adjustments can be carried out whilst the system is counting, and a calibration obtained at any desired operating frequency.

The correlator described is designed to work over a fairly small frequency range, since the phase splitter used cannot generate accurate quadrature signals over a very wide bandwidth. For our present purposes this is no limitation. Use of a phase/quadrature signal source base on a phase-locked loop would allow operation over a wider bandwidth than the present correlator, and we are investigating this alternative. It is not necessary to achieve exactly ninety degrees phase shift between the RF signals used in the correlator, since in practice a few degrees imbalance leads to a negligible error. In use, delay lines are arranged to ensure close phase matching of the drive to the excitation source modulator and the 'in-phase' RF signal driving the correlator. However, this is not crucial, since measurement of the phase and quadrature components of a known reference fluorescent sample offers a simple route to correct for a fixed instrumental phase shifts.

The correlation principle described allows accurate measurement of phase shift and demodulation ratio where the modulated excitation is not a pure sinusoid, since the correlator effectively filters out the fundamental frequency. Normally, harmonic purity of modulation is the desired goal, which is difficult to achieve at high modulation depth. An alternative is to deliberately drive the excitation source with a non-sinusoidal waveform and harmonically analyse the resulting waveform. The correlator is easily adapted to such measurements by adding additional pairs of detection channels correlated with harmonics of the RF fundamental to process photon-generated pulses in parallel.

The photomultiplier 17 is capable of decay time measurements only on a point by point basis, but could be used with an optical scanning system to generate an image (as is common with confocal microscopes using laser sources). In an alternative arrangement (not shown) a laser beam (suitably modulated) could be used as the excitation source and scanned over the full area of sample so as to obtain a complete image thereof.

In a further embodiment, the photomultiplier may be replaced by a spatially resolving detector, e.g. an Imaging Photon Detector, as shown in FIG. 5.

The arrangement of FIG. 5 is in many respects similar to that of FIG. 1 and like parts are identified by the same reference numerals. The arrangement of FIG. 5 incorporates (in place of the photomultiplier 17) an Imaging Photon Detector (IPD), e.g. as manufactured by ITL Ltd. The IPD comprises a detector head 100 and a remote electronics module, which processes signals from the head. The principles of the IPD are simple and are illustrated in FIG. 6. Photons striking a photocathode 102 produce electrons which are drawn into a stack of microchannel plate electron multipliers 103 proximity focused to the cathode. The electron burst 104 leaving the rear of the channel plate stack is accelerated and strikes an appropriately shaped resistive anode 105, which is equipped with charge sensitive preamplifiers 106 at each corner. By appropriate analogue processing it is possible to measure the position of arrival on the anode of the electron burst, since this determines the relative charge sensed by each of the preamplifiers connected to the anode. Appropriate processing electronics encodes this positional information into a digital address, subject to checks on overall pulse amplitude to eliminate noise pulses and cosmic ray events. Clearly, the digital address so generated locates the arrival point of the initial incident photon at the photocathode. In an IPD imager, the digital address is mapped into a framestore, and the corresponding memory location is incremented. Thus an image is built up over time as counts build up in the framestore. The standard IPD was modified by us to incorporate changes in internal layout of the detector head, and to include a fast preamplifier 107 connected to the rear surface of the final microchannel plate. This modification allows fast timing circuitry to register the time of arrival of each photon. It is not possible to perform sufficiently fast timing from the resistive anode of an IPD, since the high resistance gives a long time constant though other types of spatially resolving anodes (wedge-and-strip etc.) might be used in this way.

The fast timing pulses picked off from the rear of the channel plate stack are further amplified using an Ortec 454 timing filter amplifier, and trigger a constant fraction discriminator (Ortec 463). The output from this discriminator passes into a custom built electronics module, (as shown in, and described with reference to, FIG. 2) the purpose of which is to correlate the timing pulses with appropriate radio frequency signals. The correlator has two outputs. These act as 'flags', which can be independently sensed by the host computer. If a flag is set, then an offset is added to the digital address generated by the IPD head, and the memory at this location is incremented. Thus, over time three independent images accumulate in the computer. One of these is the normal intensity image seen by the IPD head. The other two images are similar, but have been processed by the correlator module.

The principles of operation of the correlator have been explained earlier. Other designs of correlator are possible, and variations and extensions to the scheme given as an example will be apparent to those skilled in the relevant areas of science and technology.

If the input to such a correlator were provided from a single photon counting tube detecting modulated light, then the integrated total pulse count from the 'quadrature' and 'in-phase' channels would represent the sine- and cosine transforms respectively for the output signal, superimposed on an average value. The probabilistic correlator is implementing the equivalent in single photon terms of multiplying an analogue signal by a sinusoid and integrating the result. If the average value of the signal is subtracted from the integrated output from each channel of the correlator, and the remainder divided, then the result gives the tangent of the phase angle between the detected signal and the reference cosine. The average value for the subtraction is simply determined by turning off the RF reference signal to the correlator. Alternatively the correlator might be equipped with an additional channel correlated in antiphase with excitation modulation, and the average of 'phase' and 'antiphase' channels could be used as the 'DC' component for subtraction.

If the detector is an IPD, then each processed photon pulse is associated with an address in a computer memory. The extension of the above correlation scheme to phase shift measurement on an image is quite straightforward. Each memory location acts as a counter, and so integrates data from one pixel of an image. The electronic processor supplied with the IPD provides a strobe pulse which indicates that data are valid. In our instrument, this strobe pulse sets a flag in an interface adapter connected to an Acorn Archimedes RISC computer.

To calculate an image weighted by phase shift, the images from 'quadrature' and 'phase' channels each are processed by subtraction of a 'DC' image (obtained either by 'phase'-'anti-phase' averaging as explained above, or by prior calculation and scaling of the uncorrelated 'intensity' image). The resulting images are then simply divided. To obtain an image weighted by demodulation, the RMS sum of the images is calculated.

FIGS. 7a and 7b provide a simplified illustration as to the manner in which the apparatus of FIG. 5 operates. Briefly, a fluorescent sample with a relatively short decay time (as indicated FIG. 7a) provides an emission signal which is almost in phase with the excitation radiation. As such the 'in phase' image is considerably stronger than the 'in quadrature' image. Conversely, a fluorescent sample with a relatively long decay time (see FIG. 7b) provides an emission signal which is relatively out of phase with the excitation radiation and attenuated with respect thereto. As such, the 'in phase' image is only slightly more intense than the 'in quadrature' image. The final image obtained from the apparatus for the sample of relatively short decay time will therefore be distinguishable from that for the sample of relatively long decay time.

Practical results obtained using the apparatus are shown in FIGS. 8 and 9.

FIG. 8 shows crystals of anthracene (decay time approx. 9 nanoseconds) alongside long needle-like crystals of POPOP (1,4 Di-[2-(5-phenyloxazoyl]benzene), which has a much shorter decay time. The approximate decay times were independently measured using a decay time microfluorometer. The correlator was operated at a frequency of 31.25 MHz for decay time imaging. The image at the top left is that accumulated by the 'quadrature' channel of the correlator, while that on the top right is the 'in-phase' image. In both cases, the anthracene emission dominates the images. The decay time-weighted image is shown below. Here the fluorescence intensity contrast is lost, and the shorter decay time species appear brightest. Consequently, the crystals of anthracene and POPOP are very clearly distinguishable.

A very similar image is shown in FIG. 9. Here, the crystals are POPOP and a fluorescent complex of europium, which has a very long decay time. At the modulation frequency used (again, 31.25 MHz), this emission is totally demodulated. The intensity contrast in the upper pair of images does not readily allow the europium complex to be distinguished from the POPOP, but the composition of the sample is obvious from the decay time-weighted image below.

There are several other ways in which decay time-weighted imaging can be accomplished in principle, using phase/demodulation techniques. One approach is to use an optical modulator preceding a camera, and to take images where the modulator is operated in phase and in quadrature with the excitation light source, as well as to accumulate an image where no modulation is applied so as to provide a measure of the average intensity to be subtracted from the modulated images. Unfortunately, this approach is difficult in practice, since standard optical modulators do not work well in imaging systems. An alternative, which we have also explored uses gain modulation or switching with an image intensifier preceding an electronic camera. A potential problem is that it is difficult to simultaneously achieve good modulation depth and linearity of modulation. This matters in so far as the exciting light is rarely modulated with a harmonically pure sinusoid. This is particularly difficult with Pockels cells working with poorly collimated light sources, such as xenon- of mercury arc lamps. Under these circumstances, the resulting image will only be a true representation of the fluorescence decay if the gain of the imaging system is varied sinusoidally, so that harmonics are averaged over time. If however the light source is sinusoidally modulated with low harmonic content (as can be achieved with lasers and directly modulated deuterium sources) the intensifier can optionally be used in a gain switched mode or modulated sinusoidally.

In the arrangement of FIG. 10, a fluorescent sample 200 is illuminated by a light source 201 (e.g. a deuterium lamp) modulated at radio-frequency by an RF source 202. An image of the sample 200 is obtained using a CCD camera 203, associated with an image intensifier 204 preceding the camera proper. A signal from the RF source 202 is supplied to the gain control of the intensifier via a phase-shifter 205 which may selectively shift the signal by 0°, 90° and 180°. The resultant signal is used to modulate the gain of the intensifier.

In operation of the arrangement in FIG. 10, the intensifier 204 may be modulated in phase with the light source 201 (i.e. 0° shift within the phase-shifter 205) for a predetermined period of time, and an image obtained using the camera 203. This image is stored in a computer. Similarly, images may be obtained with the intensifier modulated in quadrature and in anti-phase with the modulation of the light source; and the respective images stored in the computer 206. Examples of the three images (in phase, in quadrature, in anti-phase) obtained for both short decay time species are shown schematically at (a) in FIG. 10, and the corresponding images for a comparatively long decay time fluorescent species are shown at (b). With regard to the short decay time species, the strongest image is obtained when the gain is modulated in phase with the light source, an image of lesser intensity is obtained when the modulation is in quadrature, and the weakest image when the gain is in anti-phase. So far as the long decay time species are concerned, there is the same trend as before, but the differences are much less marked. Where decay time is so long as to completely demodulate emission, theoretically three identical images result.

The images are calculated as follows. In order to correct for variations of the RF phase shift or modulation depth across the intensifier photocathode (which can arise due to inhogenities such as surface resistivity and capacitance), for best performance a correction image is computed using a reference sample, such as a scattering sample, or sample of known decay time. This image is calculated by measurement of images modulating the intensifier in Phase (P), quadrature (Q) and in antiphase (A) with the excitation, and computing the resultant as $[Q-(P+A)/2]/[P-(P+A/2)]_{(xy)}$ (where the subscript (xy) implies correspondence between given pixels in each image).

A similar calculation is performed for the sample, giving $I'_{(xy)}$. The resultant corrected image is calculated as $$\frac{I'_{(xy)} - I_{(xy)}}{(1 + I'_{(xy)}I_{(xy)})}$$

This procedure gives images based on 'apparent decay time by phase shift' at the chosen frequency. Other calculations can be used to generate images weighted by demodulation, or by combinations of phase, demodulation, intensity, etc.

Figure 11A:
Figure 11B:
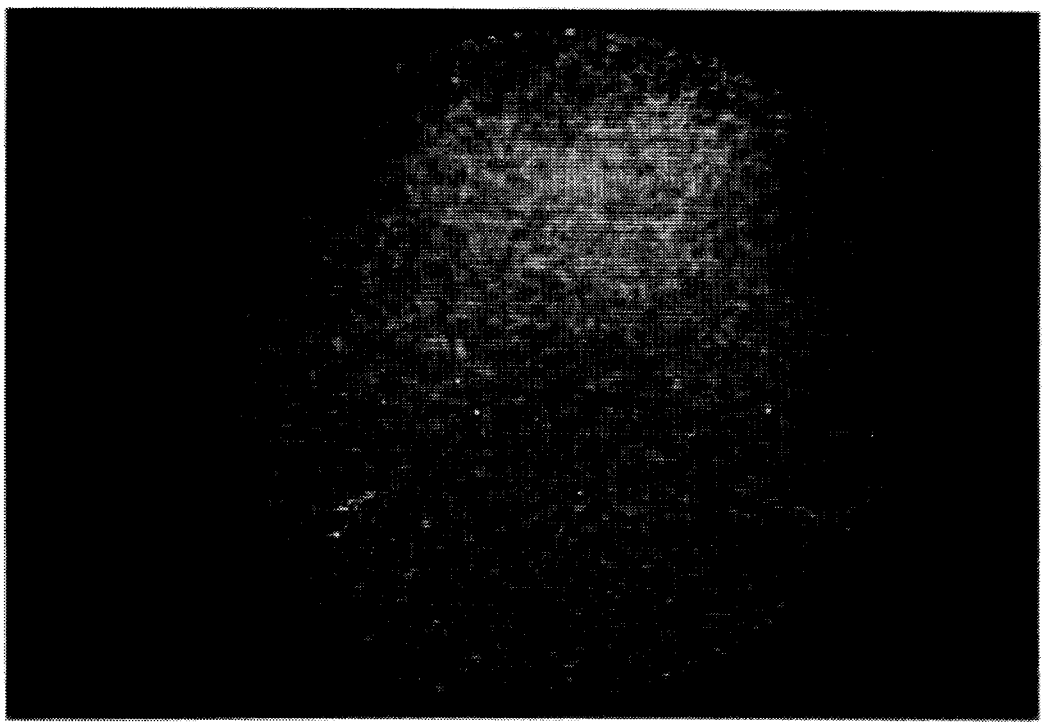
Figure 12A:
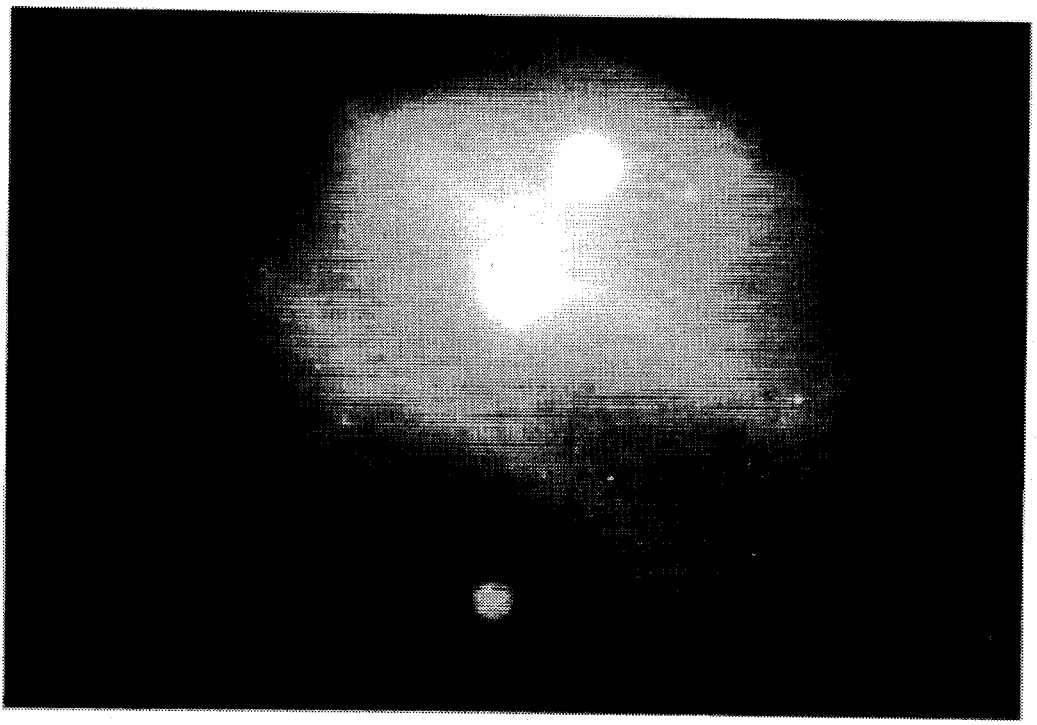
Figure 12B:
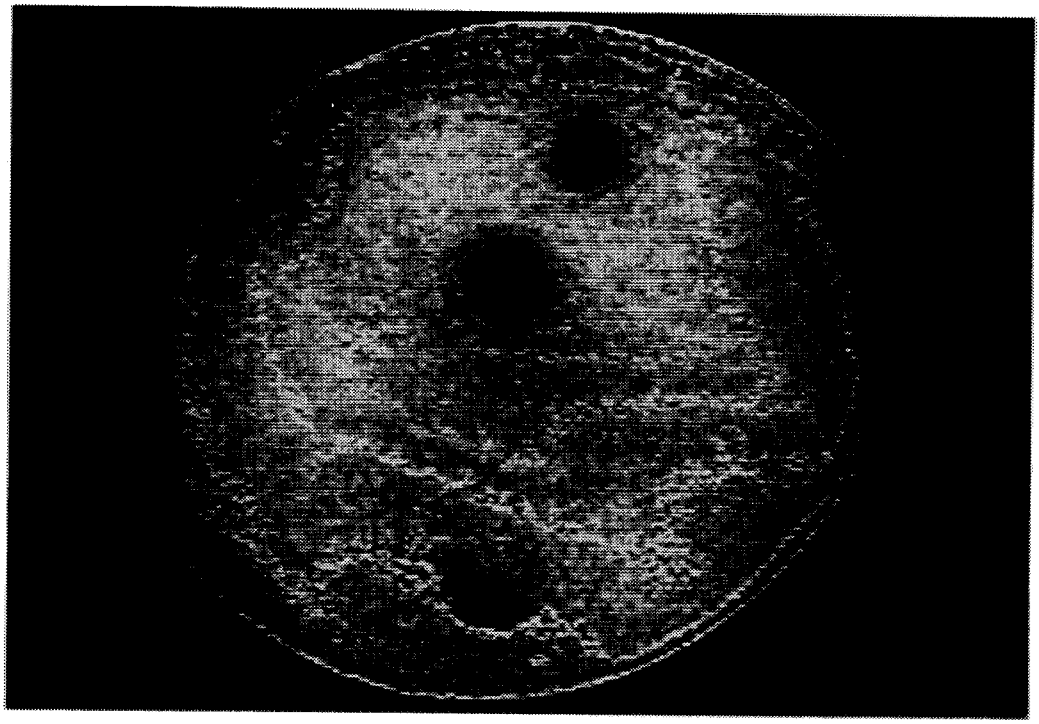

Examples of the use of the intensified CCD system are shown in FIGS. 11a and 11b and in FIGS. 12a and 12b. In FIG. 11a, an intensity image is shown of an onion epidermal layer stained with quinacrine hydrochloride. The decay time weighted image (FIG. 11b) shows no contrast, indicating a probable uniform decay time across the sample. On the other hand, FIG. 12a shows a similar picture (at higher magnification) where the onion is stained with ethidium bromide. In this case, the decay-weighted image (FIG. 12b) clearly shows a contrast between stained nuclei (where decay time is long) and the remainder of the cell.

An imaging detector based on an image intensifier is a true multichannel device, and hence offers a great multiplex advantage over any single channel device based on photomultiplier technology. We have achieved time resolved images using a custom built microchannel plate image intensifier with a conductive cathode to speed time response, and results to date have allowed images to be accumulated at modulation frequencies in excess of thirty megahertz. It seems certain that the design can be optimised to reach still higher frequencies.

Comparison of IPD and ICCD Imagers

Compared with the image using a modulated intensifier, the IPD system is inevitably slower to accumulate an image, since it is essentially a single channel device (although, of course, the output can be split for simultaneous processing at differing frequencies or reference phases). However, this disadvantage is offset by the inherent ability to achieve highly linear response, since the correlation operations are effective filters to reject harmonic distortion in the excitation light. In addition, since the heart of an IPD is essentially a microchannel plate intensifier, the time response of this device can be excellent, limited by the quality of amplifier/discriminator combination which senses the output pulse. It is simple to achieve correlation over a very wide frequency range using RF mixer technology, and this is a logical development. In addition, it is feasible to make use of inevitable harmonic distortion in the exciting light by extending the correlator to a parallel multifrequency operation. Again, the correlator design can be extended for a single frequency by using channels correlated in phase, quadrature, antiphase and antiquadrature. Such an approach optimises signal-to-noise ratio for a given accumulation time, since, in the dual channel system described here, only fifty percent of the pulses are processed for each correlation channel.

The IPD imager has obvious applications to decay time imaging, as well as to multidimensional spectroscopy of the excitation/emission matrix type, where the extra dimension of apparent decay time by phase could be added. Other workers have used an IPD system for subnanosecond timing in a conventional pulsed excitation system, and the device clearly has potential n conventional decay time fluorometry using single photon counting (7). An advantage of phase/demodulation measurements in our context is the ability to conveniently compress information in a format which is very efficient in use of computer storage, as well as allowing us the use of a conventional arc source for excitation. The ability to measure an apparent decay time by phase for a simple system working at a single modulation frequency but resolved in excitation and/or emission wavelengths might well prove valuable as an alternative to multifrequency measurements at a fixed excitation/emission wavelength. The applications of the technology to differential polarised phase fluorometry are also obvious, both in a spectroscopic sense and for imaging in biological samples.

The heart of the IPD decay time imager is the correlator module. As explained, this can equally be used with a single photon counting photomultiplier in a scanning system such as a confocal imager. Confocal laser imagers are currently very popular in biology, since they offer excellent depth discrimination. However, in order for a single channel system to equal a multichannel system in sensitivity, broadly speaking comparable light intensities must be used to illuminate samples in both instruments. In the confocal scanner, at any instant most of the sample in unilluminated, but the illuminated region is subject to extremely high light intensity. This can result in distortions to the basic photophysics of the fluorescence measurement, since the probability of processes such as triplet-triplet annihilation cannot be considered negligible under these conditions. Consequently, for linearity in quantitative confocal imaging, it is likely to prove necessary to reduce light intensity and accumulate the image more slowly than usual. Photon counting detection will probably be necessary under these circumstances, rather than gain modulation of the detector, so that the correlator should prove suitable. With this qualification, we consider that decay time measurements on confocal scanning systems should be valuable and readily implemented.

Confocal images using either the IPD or intensifier technology could be built using slit or disk scanning microscopes, since here instantaneous point source brightness can be much lower than for laser scanners, while retaining adequate sensibility.

The ability to measure fluorescence decay time in an image potentially can improve quantitation of fluorescence microscope images. If a fluorophore is dynamically quenched, so that its decay time is reduced, then measured fluorescence intensity will also be reduced. Thus, it is difficult to measure concentration profiles of fluorophores in images by intensity variations alone, since the quenching dynamics might vary from point to point on the sample. Simultaneous measurement of the decay time weighted image can correct for any such variations, though not, of course, for total static quenching of fluorescence.

References

1. Ware, W. R. 1983. *Time Resolved Fluorescence Spectroscopy in Biochemistry and Biology, NATO ASI Series A, Life Sciences* Ed. R. B. Cundall and R. E. Dale (New York: Plenum) 69A, 23.
2. Teale, F. J. W. 13 *Time Resolved Fluorescence Spectroscopy in Biochemistry and Biology, NATO ASI Series A, Life Science* Ed. R. B. Cundall and R. E. Dale (New York: Plenum) 69A, 59

3. Schlag, E. W., Selzle H.L., Schneider S. and Larsen, J. G., 1974. Single photon phase fluorometry with nanosecond time resolution. *Rev. Sci. Instrum.*, 45,
4. Murray, J. G., Cundall, R. B., Morgan, C. G., Evans, G. B and Lewis, C. 1986. A single-photon-counting Fourier transform microfluorometer. *J. Phys. E. Sci. Instrum.*, 19, 349.
5. Spencer, R. D and Weber, G. 1969. Measurements of subnanosecond fluorescence lifetimes with a cross-correlation phase fluorometer. *Ann. N.Y. Acad. Sci.*, 158, 361.
6. D. Ress, I. McWhirter, P. A. Rounce and F. E. Barlow; J. Phys. (E) 14 229 (1981).
7. W. G. McMullan, S. Charbonneau and M. L. W. Thewalt; Rev. Sci. Instrum. 58 (9) 1626 (1987).

I claim:

1. Apparatus for producing decay time weighted information of a luminescent sample, comprising:
   an excitation light source arranged to illuminate the sample;
   means for modulating the intensity of the excitation light in a predetermined cyclical manner;
   detector means for detecting photons emitted by the sample as a result of luminescence;
   means for storing data representative of detected photons, the stored data being weighted as a function of phase difference between detection of photons and the cyclically varing modulation; and
   means for producing decay time weighted information from the stored data wherein the weighted stored data is obtained using first and second reference signals each varying in the predetermined cyclical manner and having a known phase shift relative to each other.

2. Apparatus as claimed in claim 1, wherein one of the reference signals is in phase with the modulation of the light source.

3. Apparatus as claimed in claim 1, wherein the reference signals are in quadrature relative to each other.

4. Apparatus as claimed in claim 1, wherein the detector means is a spatially resolving detector.

5. Apparatus as claimed in claim 1, wherein said means for producing decay time weighted information is capable of producing a decay time weighted image.

6. Apparatus as claimed in claim 1, wherein the means for modulating the intensity of the excitation light acts on the light emitted from the source.

7. Apparatus as claimed in claim 1, wherein a Pockels cell is provided to modulate light from said source.

8. Apparatus as claimed in claim 1, wherein the light source is one which is adapted to be modulated so as to emit modulated excitation light.

9. Apparatus as claimed in claim 1, wherein the light source is a deuterium lamp.

10. Apparatus as claimed in claim 1, wherein the detector means is capable of detecting single photons and providing an output in response thereto.

11. Apparatus as claimed in claim 1, comprising means for generating at least first and second correlation signals which are out of phase with each other and which are of predetermined phase relationship relative to said modulation of the excitation light, means for correlating the output of the detector means representative of detected photons with each of said first and second signals and independently producing output signals from each said correlations if a probability function which is dependent on the position in the phase cycle at the time of the respective correlation is satisfied, said outputs from said correlations being provided to said data storage means.

12. Apparatus as claimed in claim 11, wherein the detector means is capable of providing positional information as to the position on the sample from which a detected photon was emitted, the data storage means is capable of storing first and second image representations of the sample, said representations being associated with positional addresses representative of the position on the sample at which detected photons are emitted, an output signal resulting from the correlation with the first reference signal causes the positional address corresponding to the position on the sample of the detected photon to be incremented in the first image representation and an output signal resulting from the correlation with the second reference signal causes the positional address corresponding to the position on the sample of the detected photon to be incremented in the second image representation.

13. Apparatus as claimed in claim 12, wherein the detector means is an Imaging Photon Detector.

14. Apparatus as claimed in claim 1, wherein the first reference signal is in phase with the modulation of the excitation light and the second reference signal is in quadrature with the modulation of the excitation light.

15. Apparatus as claimed in claim 1, wherein the means for detecting photons comprises an electronic camera associated with an image intensifier and means are provided for cyclically modulating the gain of the intensifier under two different conditions which are out of phase with each other and which have a predetermined phase relationship relative to the modulation of the excitation light.

16. Apparatus as claimed in claim 15, wherein a first condition for modulating the gain of the intensifier is in phase with the modulation of the excitation light and the other condition is in quadrature relative thereto.

17. Apparatus as claimed in claim 16, wherein the means for cyclically modulating the gain of the intensifier is additionally capable of modulating said gain in anti-phase relationship with the modulation of the excitation light.

18. Apparatus as claimed in claim 15, wherein the means for producing decay time weighted information includes means for using a reference image of known properties to correct for spatial inhomogeneity of the properties of the detector means.

19. Apparatus as claimed in claim 1, wherein the excitation light is modulated at Radio Frequency.

20. Apparatus for producing decay time weighted information of a luminescent sample, comprising:
   an excitation light source arranged to illuminate the sample;
   means for pulsing the intensity of the excitation light in a predetermined cyclical manner; detector means for detecting photons emitted by the sample as a result of luminescences;
   means for storing data representative of detected photons, the stored data being weighted as a function of phase difference between detection of photons and the cyclically varying modulation; and
   means for producing decay time weighted information from the stored data.

* * * * *